(12) United States Patent
Pushpangadan et al.

(10) Patent No.: US 7,482,031 B2
(45) Date of Patent: Jan. 27, 2009

(54) DEVELOPMENT OF AN ANTI-COUGH, ANTI-TUSSIVE AND THROAT SOOTHING HERBAL FORMULATION

(75) Inventors: Palpu Pushpangadan, Uttar Pradesh (IN); Govindarajan Raghavan, Uttar Pradesh (IN); Vijayakumar Madhavan, Uttar Pradesh (IN); Shanta Mehrotra, Uttar Pradesh (IN); Rawat Ajay Kumar Singh, Uttar Pradesh (IN); Chandana Venkateshwara Rao, Uttar Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 545 days.

(21) Appl. No.: 10/457,182

(22) Filed: Jun. 9, 2003

(65) Prior Publication Data

US 2004/0126441 A1  Jul. 1, 2004

Related U.S. Application Data

(63) Continuation of application No. PCT/IB02/05654, filed on Dec. 30, 2002.

(51) Int. Cl.
| A61K 47/00 | (2006.01) |
| A61K 9/68  | (2006.01) |
| A61K 36/00 | (2006.01) |
| A61K 36/67 | (2006.01) |

(52) U.S. Cl. ........................ 424/734; 424/439; 424/441; 424/725

(58) Field of Classification Search .................. None
See application file for complete search history.

(56) References Cited

U.S. PATENT DOCUMENTS

| 5,436,329 | A  | * | 7/1995  | Caboche ..................... 536/103 |
| 5,830,884 | A  | * | 11/1998 | Kasica et al. ................ 514/160 |
| 6,080,401 | A  | * | 6/2000  | Reddy et al. ................ 424/93.3 |
| 6,432,441 | B1 | * | 8/2002  | Bealin-Kelly et al. ....... 424/440 |
| 2003/0228383 | A1 | * | 12/2003 | Doshi et al. ................. 424/734 |

* cited by examiner

*Primary Examiner*—S. Tran
(74) *Attorney, Agent, or Firm*—Merchant & Gould P.C.

(57) ABSTRACT

An anti-cough, anti-tussive, and throat soothing synergistic herbal formulation comprising of an extract of *Piper cubeba, Glycyrrhiza glabra, Acorus calamus Alpinia galanga, Zingiber officinale* and pharmaceutically acceptable additives as a syrup, lozenges or chewable tablets for preventing cracking of voice, dryness of mouth and toning of voice, vocal cord; the present invention also provides a method of preparation of this formulation.

36 Claims, No Drawings

DEVELOPMENT OF AN ANTI-COUGH, ANTI-TUSSIVE AND THROAT SOOTHING HERBAL FORMULATION

FIELD OF THE INVENTION

The present invention relates to development of an anti-cough, anti-tussive and throat soothing herbal formulation(s).

BACKGROUND ART

Anti-tussives are substances that specifically inhibit or suppress the act of coughing. Such inhibition may be due to (1) depression of medullary center or associated higher centers (2) increased threshold of periphery reflexogenous zones (3) interruption of tussal impulses in the afferent limb of cough reflex (4) inhibition of conduction along the motor pathways and (5) removal of irritants by facilitating bronchial drainage and mucociliary activity.

Wide arrays of antitussive combinations are commercially available. The combinations can consist of two to four active ingredients and include any combination of an antitussive plus sympathomimetics, antihistamines, expectorants and/or analgesics. These cough products are very controversial and rarely offer an advantage.

The over-the-counter (OTC) market has offered products for throat soothing for many years. Majorities of these products utilize phenol as their active ingredient. Phenol is the simple alcohol derivative of benzene. Both of these chemicals are listed by the Environmental Protection Agency (EPA) as extremely carcinogenic.

Histamine is an endogenous mediator and plays an important role in bronchoconstriction. Mainly it acts through different receptors in the bronchial muscle. The histamine is stored in the mast cells during stress or abnormal physiological function, the mast cell degranulates and the histamine is released. The mediator histamine is playing a key role in the cough and throat infections.

A natural non-carcinogenic formulation for treatment of cough, soothing of throat is an alternative of phenol especially for the speakers, who need to speak for a longer duration of time, to prevent the breakdown of voice and dryness of the mouth. Hitherto, an herbal formulation is the need of the hour having throat soothing activity along with prevention of dryness of mouth and breaking of voice. Only on oral tradition prevalent in certain group of South Indian Brahmin (Aiyangar) particularly those families who participate in vedic recital for days together, (one of the authors of this patent is from one such family) we have proposed an entirely novel formulation(s). These people use *Piper cubeba* for clearing throats and to maintain a healthy and sound vocal system, while they recite veda continuously for over a week. Based on this lead we propose a novel formulation(s) in a combination with a better dosage form and activity.

As a result of intensive study conducted by the inventors, with the aim of achieving aforementioned objectives, new formulations for oral ingestion were developed employing herbal drugs which are from natural origin, incorporating them into binders and diluting agents to form oral dosage forms.

OBJECTS OF THE INVENTION

The primary objective of the invention is to prepare a novel anti-tussive and throat soothing herbal formulation(s), which prevents dryness of mouth, and cracking of voice by toning the vocal cord.

Another objective of the present invention is to prepare a formulation(s) that gives immediate relief to throat irritation and also stimulates the release of saliva.

Yet another of the present invention is to prepare herbal formulation with a combination of the plants which are used in bronchitis, asthma, stimulate respiration, bronchodialator, antimicrobial, antitussive along with antiemetic anti-inflammatory, bronchial catarrh properties and also in the treatment of allergic reactions.

SUMMARY OF THE INVENTION

In accordance with the present invention a synergistic herbal composition is provided to prevent dryness of the mouth, cracking of voice, soreness of throat that contains *Piper cubeba* that has been used by a certain group of people as mentioned in the prior art for the above mentioned purpose as the active ingredient. Along with these plants other traditional plants like *Glycyrrhiza glabra, Acorus calamus, Alpinia galanga* and *Zingiber officinale* are added which are used in bronchitis, asthma, to stimulate respiration, antimicrobial, antitussive and also in the treatment of allergy.

DETAILED DESCRIPTION OF THE INVENTION

Accordingly, the present invention provides an anti-cough, anti-tussive, and throat soothing synergistic herbal formulation, which prevents dryness of mouth, and cracking of voice by toning the vocal cord, the said formulation comprising of:

| INGREDIENTS | wt./wt. % |
| --- | --- |
| a) an extract of *Piper cubeba* | 0.5 to 2.0 |
| b) an extract of *Glycyrrhiza glabra* | 0.5 to 2.0 |
| c) an extract of *Acorus calamus* | 0.01 to 0.1 |
| d) an extract of *Alpinia galanga* | 0.01 to 0.1 |
| e) an extract of *Zingiber officinale* | 0.01 to 0.1 |
| f) pharmaceutically acceptable additives | 95.7 to 98.97 |

An embodiment of the present invention provides a formulation that may be administered in oral dosage form as a syrup, lozenges, or chewable tablets.

Another embodiment of the present invention provides a formulation in which the syrup used may contain 60 to 80% sugar of the total formulation.

Still another embodiment of the present invention provides a formulation in which the syrup used may contain 6 to 8% of aspertame for diabetic patients.

Still another embodiment of the present invention provides a formulation in which the lozenges used contains sugar candy.

Yet another embodiment of the present invention provides a formulation wherein the extract of plants used is obtained by extraction with 50% aqueous alcoholic solution.

Still another embodiment of the present invention provides a formulation in which the alcohol used is ethanol.

Yet another embodiment of the present invention provides a formulation in which the total wt % of the plant extracts used ranges between 1.03 to 4.3 of the total formulation.

Still another embodiment of the present invention provides a formulation in which the extract of *Piper cubeba* used is a fruit extract.

Another embodiment of the present invention provides a formulation in which the plant extracts used may be obtained from the plant parts selected from fruit, rhizome or root parts.

Still another embodiment of the present invention provides a formulation, in which the pharmaceutically acceptable additives used are selected, from binder, diluent, lubricant, glidant or disintegrant.

Yet another embodiment of the present invention provides a formulation in which the diluents used are lactose, starches; sugars such as mannitol, sorbitol, xylitol, dextrose, sucrose; microcrystalline cellulose; basic calcium phosphate; calcium sulfate or mixtures thereof.

Still another embodiment of the present invention provides a formulation in which the binders used are starch paste, sorbitol, alginates, polyvinyl pyrrolidone, gum acacia, cellulose derivatives such as hydroxypropylmethyl cellulose, hydroxypropyl cellulose, methyl cellulose, carboxymethyl cellulose, methylcellulose, ethylcellulose, pregelatinized starch, tragacanth or mixtures thereof.

Yet another embodiment of the present invention provides a formulation in which the glidants used are silica derivatives, talc, starch or mixtures thereof.

Another embodiment of the present invention provides a formulation in which the lubricant used are selected from metallic stearates, stearic acid, talc, polyethylene glycols, soluble salts such as sodium chloride, sodium benzoate, sodium lauryl sulfate, spray dried magnesium lauryl sulfate, boric acid, starch, lactose or mixtures thereof.

In yet another embodiment, the binder used may be either starch or gum acacia or natural binders like tragacanth.

In still another embodiment, the diluent used to make up the dosage form may be lactose.

In still another embodiment, formulation(s) prevents dryness of mouth and cracking of voice by toning the vocal cord.

In an embodiment, the formulation is used as an antispasmodic and expectorant In another embodiment, the formulation immediately relieves throat irritation by acting as a soothing agent.

In still another embodiment, the mast cell regeneration was found to be 20.2±3.1–59.3+5.2.

Yet another embodiment of the present invention provides a formulation, which is non-toxic and in which no mortality is observed.

Still another embodiment of the present invention provides a formulation, which has anti-spasmodic, expectorant and throat soothing properties.

One more embodiment of the present invention provides a method of preparing a formulation, wherein the said method comprises steps of:
 a. obtaining the required part of medicinal plants,.
 b. drying the plant material of step (a) in shade,
 c. powdering the dried plant material of step (b) to obtain a fine powder,
 d. extracting the powdered plant material of step (c) with aqueous alcohol at a temperature range of 25-35° C. for a time period of 4 to 7 days to obtain an aqueous alcoholic extract,
 e. concentrating the extract of step (d) under reduced pressure at a temperature range of 40-60° C. to obtain a concentrated extract,
 f. lyophilising the concentrated extract of step (e) for complete removal of solvent to obtain the required plant extract, and
 g. formulating the plant extract of step (f) with suitable pharmaceutically acceptable additives to obtain the required formulation.

Another embodiment of the present invention provides a method of preparation of a formulation wherein the formulation obtained may be administered orally in a dosage form as syrup, lozenges, or chewable tablets.

Another embodiment of the present invention provides a method of preparation of a formulation in which the syrup used may contain 60 to 80% sugar of the total formulation.

Still another embodiment of the present invention provides a method of preparation of a formulation in which the syrup used may contain 6 to 8% of aspartame for diabetic patients.

Yet another embodiment of the present invention provides a method of preparation of a formulation in which the lozenges used contain sugar candy.

Still another embodiment of the present invention provides a method of preparation of a formulation in which the aqeuous alcohol solution used is 50% aqeous alcohol.

Yet another embodiment of the present invention provides a method of preparation of a formulation in which the alcohol used is ethanol.

Another embodiment of the present invention provides a method of preparation of a formulation in which the total wt % of the plant extract obtained ranges between 1.03 to 4.3 of the total formulation.

Still another embodiment of the present invention provides a method of preparation of a formulation in which the pharmaceutically acceptable additives used are selected from a group consisting of binder, diluent, lubricant, glidant, disintegrant or mixtures thereof.

Another embodiment of the present invention provides a method of preparation of a formulation in which the diluents used are selected from lactose; starches; sugars such as mannitol, sorbitol, xylitol, dextrose, sucrose; microcrystalline cellulose; basic calcium phosphate; calcium sulfate or mixtures thereof.

Still another embodiment of the present invention provides a method of preparation of a formulation in which the binders used are selected from starch paste, sorbitol, alginates, polyvinyl pyrrolidone, gum acacia, cellulose derivatives such as hydroxypropylmethyl cellulose, hydroxypropyl cellulose, methyl cellulose, carboxymethyl cellulose, methylcellulose, ethylcellulose, pregelatinized starch, or mixtures thereof.

Yet another embodiment of the present invention provides a method of preparation of a formulation in which the glidants used are selected from silica derivatives, talc, starch or mixtures thereof.

Still another embodiment of the present invention provides a method of preparation of a formulation in which the lubricants used are selected from metallic stearates; stearic acid; talc; polyethylene glycols; soluble salts such as sodium chloride, sodium benzoate, sodium lauryl sulfate; spray dried magnesium lauryl sulfate; boric acid, starch; lactose or mixtures thereof.

Yet another embodiment of the present invention provides use of a formulation for preventing dryness of mouth, cracking of voice and sustaining of voice.

Another embodiment of the present invention provides use of a formulation for toning of voice and vocal cord.

Another embodiment of the present invention provides use of a formulation in treating bronchial catarrh and allergic reactions in throat.

Still another embodiment of the present invention provides use of a formulation which when used orally in rats for six days does not affect the body weight, kidney, liver and spleen.

Another embodiment of the present invention provides use of a formulation, which gives mast cell regeneration in the % range of 20.2+3.1 to 59.3+5.2.

The novelty of the present investigation is (1) herbal formulation for the prevention of dryness of mouth and cracking of voice by toning of the vocal cord (2) the herbal formulation which is an antitussive, anticough and has throat soothing property (3) the herbal formulation gives immediate relief to throat irritation (4) unlike the commercial antitussive combinations, the herbal formulation maintains the vocal cord.

Each formulation has been described in detail giving the formula of the ingredients along with the method of preparation.

The first step in the preparation of these formulations involves a process for making, the plant material suitable for formulating into a syrup, lozenges or chewable tablets. The specified portion of the plant is collected and dried under shade at room temperature (25-35° C.) for 60-72 hours or until the material gets dried. The material is then powdered into a fine powder. A specified amount of the powdered material is then extracted exhaustively with 50% aqueous alcohol at room temperature (25-35° C.). Extraction was carried out in a closed container immersing specified amount of the plant material in specified solvent (1:8-1:15 ratio) for 4-7 days. At the end of this stage, solvent is decanted and filtered if necessary to make it free from plant debris. The solvent is then concentrated by evaporating under vacuum at less than 40-60° C. The concentrate is then freeze dried to obtain final product in powder form. The final product is then made into oral dosage form by using it as an ingredient for making syrup, lozenges or chewable tablets. Suitable binders like starch and diluents like lactose are added to make up the formulation. Simple syrup as mentioned in Indian Pharmacopoeia is taken for making the syrup formulation.

The following examples are for illustration purpose only and should not be construed to limit the scope of the invention

EXAMPLES

Example—1

| *Piper cubeba* | 2 wt. % |
| *Glycyrrhia glabra* | 2 wt. % |
| *Acorus calamus* | 0.1 wt. % |
| *Alpinia galanga* | 0.1 wt. % |
| *Zingiber officinale* | 0.1 wt. % |
| Sucrose | 66.7 g |
| Alcohol | 10 wt. % |
| Water | q.s. to make 100 ml |

*Piper cubeba, Glycyrrhiza glabra, Acorus calamus, Alpinia galanga* and *Zingiber officinale* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Mix the plant extracts and dissolve them in 500 ml 10% alcohol, filter the solution and add specified quantity of sugar and heat the until the sugar dissolves and then cool and make up the volume with required amount of water to make 100 ml.

The formulation is useful to prevent dryness of mouth and cracking of voice and is an antitussive.

Mast Cell Stabilization Activity

Rats were prior treated with 1 ml, 2 ml, 4 ml, and 6 ml to different groups and 3 hours after last dose treatment. Rats were sacrified and intestinal mesentry was taken for study of mast cells. Mesnteries of sacrified rats along with intestinal pieces were kept in a Ringer's solution at 37° C.

Pieces of mesentry were stained with Toludiene blue (0.1% for 10 min), then the tissue was then transferred to xylene for 5-10 min. and finally rinsed 2 or 3 times with acetone.

The intestinal tissue pieces were out and removed, placed in a slide and stretched with the help of needles. Then, the tissue was examined under the microscope. The numbers of intact and disrupted mast cells per high field (400×) were counted.

Example—2

| *Glycyrrhia glabra* | 1.5 wt. % |
| *Acorus calamus* | 0.12 wt. % |
| *Alpinia galanga* | 0.15 wt. % |
| *Zingiber officinale* | 0.05 wt. % |
| Sucrose | 66.7 g |
| Alcohol | 10 wt. % |
| water | q.s. to make 100 ml |

*Glycyrrhiza glabra, Acorus calamus, Alpinia galanga* and *Zingiber officinale* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Mix the plant extracts and dissolve them in 500 ml 10% alcohol, filter the solution and add specified quantity of sugar and heat the until the sugar dissolves and then cool and make up the volume with required amount of water to make 100 ml.

The formulation is useful as an expectorant.

Example—3

| *Piper cubeba* | 1 wt. % |
| *Glycyrrhia glabra* | 0.5 wt. % |
| *Acorus calamus* | 0.1 wt. % |
| *Alpinia galanga* | 0.06 wt. % |
| *Zingiber officinale* | 0.07 wt. % |
| Sugar | 70 wt. % |
| Gum acacia | 7 wt. % |
| Water | q.s. |

*Piper cubeba, Glycyrrhiza glabra, Acorus calamus, Alpinia galanga* and *Zingiber officinale* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Powdered drug, powdered sugar, and powdered gum is taken and water is slowly added to form a pliable mass. The mass is rolled out and is cut into pieces using a cutter. Each piece is shaped and allowed to dry before dispensed.

The formulation is useful to prevent dryness of mouth and cracking of voice and is an antitussive.

Example—4

| | |
|---|---|
| *Piper cubeba* | 1.5 wt. % |
| *Glycyrrhia glabra* | 0.5 wt. % |
| *Acorus calamus* | 0.01 wt. % |
| *Alpinia galanga* | 0.05 wt. % |
| *Zingiber officinale* | 0.05 wt. % |
| Alcohol | 10 wt. % |
| Syrup | q.s. |

*Piper cubeba, Glycyrrhiza glabra, Acorus calamus, Alpinia galanga* and *Zingiber officinale* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Syrup is concentrated to an extent that it becomes a pliable mass and then active ingredient is added and the mixture is kneaded while it is warm to form a homogenous mass. The mass is worked gradually worked into a tube and then cooled and then cut into pieces and dispensed.

The formulation is useful to prevent dryness of mouth and cracking of voice and is an antitussive.

Example—5

| | |
|---|---|
| *Piper cubeba* | 2 wt. % |
| *Glycyrrhia glabra* | 1.5 wt. % |
| *Acorus calamus* | 0.05 wt. % |
| *Alpinia galanga* | 0.05 wt. % |
| *Zingiber officinale* | 0.05 wt. % |
| Polyvinyl pyrrolidine | 2% |

*Piper cubeba, Glycyrrhiza glabra, Acorus calamus, Alpinia galanga* and *Zingiber officinale* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilized to obtain the extract in powder form. The ingredients are mixed along with PVP and compressed directly in a tableting machine using more pressure to form hard tablets.

The formulation is useful to prevent dryness of mouth and cracking of voice and is an antitussive, gives immediate relief to throat irritation.

Advantages

1. Herbal composition, which prevents the dryness of mouth, cracking of voice and throat soothing, hence will be beneficial for speakers.
2. It also prevents soreness of throat and is useful as anti-cough and antitussive.
3. It is also useful in toning of voice and vocal cord.

References:
1. U.S. Pat. No. 6,432,441 August 2002 Bealin-Kelly, et al.
2. U.S. Pat. No. 6,159,473 December 2000 Watkins, et al.
3. Remington, The science and practice of pharmacy, 19$^{th}$ edition, Vol II. pp. 974,1393, 1995
4. Agarwal et al. Indian J. Exp. Biol. 38: pp. 994-998. 2000.
5. Anonymous. Indian Pharmacopoeia. Govt of India, 1996.
6. Johri et al. Ind. J. Physiol. Pharmacol. 29(1), pp. 43-46, 1983

TABLE 1

Effect of cough syrup on percentage of degranulated and intact mast cells in rat intestinal mesentry

| Group (%) | Treatment | Intact mast cells (%) | Degranulated mast cells |
|---|---|---|---|
| 1. | Control | 18.02 ± 2.1 | 80.1 ± 5.6 |
| 2. | Piper cubeba | 38.05 ± 2.8$^c$ | 59.6 ± 6.2$^a$ |
| 3. | Syrup 1 ml | 40.02 ± 4.0$^c$ | 59.3 ± 5.2$^a$ |
| 4. | Syrup 2 ml. | 50.0 ± 4.2$^c$ | 49.7 ± 4.8$^c$ |
| 5. | Syrup 4 ml. | 64.0 ± 5.5$^c$ | 35.6 ± 4.1$^c$ |
| 6. | Syrup 6 ml | 78.0 ± 6.5$^c$ | 20.2 ± 3.1$^c$ |

Values are mean ± SEM, n = 6
P $^a$ < 0.05 and $^c$ < 0.001 compared to respective control groups.
Note:
No mortality/no gross abnormality was found in any of the treated group.
The designed formulation showed dose dependent and significant (p: < 0.05 to P < 0.001) significant protection were found in release of histamine (bronchoconstructor) from the mast cells.

TABLE 2

Effect of cough syrup on relative mean ± SEM organ weights of adult male rats (n = 6).

| Type of treatment | Treatment group | Body weight (g) | Kidney (g) | Liver (g) | Spleen (g) |
|---|---|---|---|---|---|
| 6 days oral treatment | Control | 152.8 ± 10.2 | 0.93 ± 0.05 | 5.81 ± 0.43 | 0.65 ± 0.05 |
| | Syrup (4 ml) | 156.2 ± 11.0 | 0.95 ± 0.06 | 5.88 ± 0.59 | 0.67 ± 0.04 |
| | Syrup (6 mL) | 155.5 ± 10.8 | 0.94 ± 0.06 | 5.92 ± 0.47 | 0.71 ± 0.1 |

Note:
No mortality/gross abnormality was observed in the animals during the exposure of the syrup.

The invention claimed is:

1. An herbal formulation, consisting of:

| INGREDIENTS | wt./wt. % |
|---|---|
| an extract of *Piper cubeba* | 0.5 to 2.0 |
| an extract of *Glycyrrhiza glabra* | 0.5 to 2.0 |
| an extract of *Acorus calamus* | 0.01 to 0.1 |
| an extract of *Alpinia galanga* | 0.01 to 0.1 |

-continued

| INGREDIENTS | wt./wt. % |
| --- | --- |
| an extract of *Zingiber officinale* | 0.01 to 0.1 and |
| pharmaceutically acceptable additives | 95.7 to 98.97. |

2. The formulation of claim 1 in the form of syrup, lozenge, or chewable tablet.

3. The formulation of claim 1, wherein the pharmaceutically acceptable additive is 60% to 80% sugar.

4. The formulation of claim 1, wherein the extract of *Piper cubeba*, the extract of *Glycyrrhiza glabra*, the extract of *Acorus calamus*, the extract of *Alpinia galanga*, or the extract of *Zingiber officinale* is a 50% aqueous alcohol extract.

5. The formulation of claim 4, wherein the alcohol is ethanol.

6. The formulation of claim 1, wherein the extract of *Piper cubeba* is a fruit extract.

7. The formulation of claim 1, wherein the extract of *Piper cubeba*, the extract of *Glycyrrhiza glabra*, the extract of *Acorus calamus*, the extract of *Alpinia galanga*, or the extract of *Zingiber officinale* is an extract of fruit, rhizome, root, or mixture thereof.

8. The formulation of claim 1, wherein the pharmaceutically acceptable additive is binder, diluent, lubricant, gildant, disintegrant, or mixture thereof.

9. The formulation of claim 8, wherein the diluent is lactose, starch, sugar, microcrystalline cellulose, basic calcium phosphate, calcium sulfate, or mixture thereof.

10. The formulation of claim 8, wherein the binder is starch paste, sorbitol, alginate, polyvinyl pyrrolidone, gum acacia, cellulose derivative, pregelatinized starch, tragacanth, or mixture thereof.

11. The formulation of claim 8, wherein the glidant is silica derivative, talc, starch, or mixture thereof.

12. The formulation of claim 8, wherein the lubricant is metal stearate, stearic acid, talc, a polyethylene glycol, a soluble salt boric acid, starch, lactose, or mixture thereof.

13. The formulation of claim 1, wherein the formulation is non-toxic.

14. The formulation of claim 1, wherein the formulation provides anti-spasmodic, expectorant and throat soothing properties.

15. A method of preparing an herbal formulation, the herbal formulation consisting of:

| INGREDIENTS | wt./wt. % |
| --- | --- |
| an extract of *Piper cubeba* | 0.5 to 2.0 |
| an extract of *Glycyrrhiza glabra* | 0.5 to 2.0 |
| an extract of *Acorus calamus* | 0.01 to 0.1 |
| an extract of *Alpinia galanga* | 0.01 to 0.1 |
| an extract of *Zingiber officinale* | 0.01 to 0.1 and |
| pharmaceutically acceptable additive | 95.7 to 98.97; | the method comprising:
obtaining plant material;
drying the plant material in shade;
powdering the dried plant material;
extracting the powdered plant material with aqueous alcohol at a temperature of 25-35° C. for 4 to 7 days to obtain an aqueous alcoholic extract;
concentrating the extract under reduced pressure at a temperature of 40-60 ° C. to obtain a concentrated extract,
lyophilising the concentrated extract to obtain plant extract, and
formulating the plant extract pharmaceutically acceptable additive to obtain the herbal formulation.

16. The method of claim 15, wherein formulating is producing syrup, lozenge, or chewable tablet.

17. The formulation of claim 15, wherein the pharmaceutically acceptable additive is 60% to 80% sugar.

18. The method of claim 15, wherein extracting is extracting with 50% aqueous alcohol.

19. The method of claim 18, wherein the alcohol is ethanol.

20. The method of claim 15, wherein the pharmaceutically acceptable additive is binder, diluent, lubricant, glidant, disintegrant, or mixture thereof.

21. The method of claim 20, wherein the diluent is lactose, starch, sugar, microcrystalline cellulose, basic calcium phosphate, calcium sulfate, or mixture thereof.

22. The method of claim 20, wherein the binder is starch paste, sorbitol, alginate, polyvinyl pyrrolidone, gum acacia, cellulose derivative, pregelatinized starch, tragacanth, or mixture thereof.

23. The method of claim 20, wherein the glidant is silica derivative, talc, starch, or mixture thereof.

24. The method of claim 20, wherein the lubricant is metal stearate, stearic acid, talc, a polyethylene glycol, a soluble salt boric acid, starch, lactose, or mixture thereof.

25. A method for soothing a throat in a subject in need thereof, comprising:
administering to the subject an herbal formulation;
the herbal formulation consisting of:

| INGREDIENTS | wt./wt. % |
| --- | --- |
| an extract of *Piper cubeba* | 0.5 to 2.0 |
| an extract of *Glycyrrhiza glabra* | 0.5 to 2.0 |
| an extract of *Acorus calamus* | 0.01 to 0.1 |
| an extract of *Alpinia galanga* | 0.01 to 0.1 |
| an extract of *Zingiber officinale* | 0.01 to 0.1 and |
| pharmaceutically acceptable additive | 95.7 to 98.97. |

26. The method of claim 25, comprising soothing a vocal cord.

27. The method of claim 25, comprising soothing an inflamed throat.

28. The method of claim 25, comprising soothing a throat irritated by allergies.

29. The formulation of claim 9, wherein the sugar is mannitol, sorbitol, xylitol, dextrose, sucrose, or mixture thereof.

30. The method of claim 21, wherein the sugar is mannitol, sorbitol, xylitol, dextrose, sucrose, or mixture thereof.

31. The formulation of claim 10, wherein the cellulose derivative is hydroxypropylmethyl cellulose, hydroxypropyl cellulose, methyl cellulose, carboxymethyl cellulose, methylcellulose, ethylcellulose, or mixture thereof.

32. The method of claim 22, wherein the cellulose derivative is hydroxypropylmethyl cellulose, hydroxypropyl cellulose, methyl cellulose, carboxymethyl cellulose, methylcellulose, ethylcellulose, or mixture thereof.

33. The formulation of claim 12, wherein the soluble salt is sodium chloride, sodium benzoate, sodium lauryl sulfate, spray dried magnesium lauryl sulfate, or mixture thereof.

34. The method of claim 24, wherein the soluble salt is sodium chloride, sodium benzoate, sodium lauryl sulfate, spray dried magnesium lauryl sulfate, or mixture thereof.

35. The method of claim 15, wherein powdering comprises producing a fine powder.

36. The method of claim 15, wherein lyophilizing comprises completely removing solvent.

* * * * *